United States Patent
Paulsen

(10) Patent No.: US 10,499,573 B1
(45) Date of Patent: Dec. 10, 2019

(54) WIRELESS SOIL PROFILE MONITORING APPARATUS AND METHODS

(71) Applicant: Keith Lynn Paulsen, Centerville, UT (US)

(72) Inventor: Keith Lynn Paulsen, Centerville, UT (US)

(73) Assignee: Keith Lynn Paulsen, Centerville, UT (US)

( * ) Notice: Subject to any disclaimer, the term of this patent is extended or adjusted under 35 U.S.C. 154(b) by 0 days.

(21) Appl. No.: 16/194,205

(22) Filed: Nov. 16, 2018

Related U.S. Application Data

(63) Continuation-in-part of application No. 15/156,269, filed on May 16, 2016, now Pat. No. 10,228,340.

(51) Int. Cl.
| | |
|---|---|
| *A01G 25/16* | (2006.01) |
| *A01B 63/16* | (2006.01) |
| *A01C 21/00* | (2006.01) |
| *G01N 21/3563* | (2014.01) |
| *A01B 63/02* | (2006.01) |
| *G01N 27/22* | (2006.01) |
| *G01N 33/24* | (2006.01) |
| *G01K 1/16* | (2006.01) |
| *A01B 79/00* | (2006.01) |
| *A01C 7/20* | (2006.01) |
| *G01N 21/3554* | (2014.01) |

(52) U.S. Cl.
CPC ............ *A01G 25/167* (2013.01); *A01B 63/02* (2013.01); *A01B 63/16* (2013.01); *A01C 21/007* (2013.01); *G01N 21/3563* (2013.01); *G01N 27/223* (2013.01); *A01B 79/005* (2013.01); *A01C 7/203* (2013.01); *G01K 1/16* (2013.01); *G01N 21/3554* (2013.01); *G01N 33/246* (2013.01); *G01N 2033/245* (2013.01)

(58) Field of Classification Search
CPC .... A01G 25/16; A01G 25/167; G01N 27/048; G01N 27/22; G01N 27/223; G01N 27/225; G01N 27/227; G01N 27/228; G01N 33/246; G01N 2033/245; G01R 27/2605
USPC ...... 137/78.2, 78.3; 324/658, 663, 664, 677, 324/678, 679, 686, 689, 690
See application file for complete search history.

(56) References Cited

U.S. PATENT DOCUMENTS

| | | | |
|---|---|---|---|
| 3,774,237 | A | 11/1973 | Hardway |
| 5,424,649 | A | 6/1995 | Gluck |
| 5,730,165 | A | 3/1998 | Philipp |
| 5,804,976 | A | 9/1998 | Gaskin |
| 5,859,536 | A | 1/1999 | Stockton |
| 6,194,903 | B1 | 2/2001 | Schulz |
| 6,949,937 | B2 | 9/2005 | Knoedgen |
| 7,030,630 | B2 | 4/2006 | Haas |
| 7,845,224 | B2 | 12/2010 | Barlesi |
| 7,944,220 | B2 | 5/2011 | Lock |

(Continued)

OTHER PUBLICATIONS

Kmalesh Kumar Singh and Neerah K. Chasta, Experimental Electrical Modeling of Soil or In Situ Soil Moisture Measurement, 2013 International Symposium on Electronic System Design, published on or before 2013, pp. 123-127; published by the Institute of Electrical and Electronics Engineers (shown in attachment 1).

(Continued)

*Primary Examiner* — Steven L Yeninas
(74) *Attorney, Agent, or Firm* — Austin Rapp

(57) ABSTRACT

An in situ low-power wireless measurement apparatus and method suitable for reporting a soil moisture profile at various zones.

18 Claims, 7 Drawing Sheets

(56) References Cited

U.S. PATENT DOCUMENTS

| | | |
|---|---|---|
| 10,228,340 B2 | 3/2019 | Paulsen |
| 2004/0004488 A1 | 1/2004 | Baxter |
| 2005/0068045 A1 | 3/2005 | Inaba |
| 2008/0211521 A1 | 9/2008 | Lock |
| 2013/0233707 A1 | 9/2013 | Kato |
| 2015/0160148 A1 | 6/2015 | Stanley |
| 2015/0253372 A1 | 9/2015 | Watanabe |

OTHER PUBLICATIONS

Office Action, U.S. Appl. No. 15/156,269, dated Apr. 4, 2018 (shown in attachment 2).
Supplemental Office Action Response, U.S. Appl. No. 15/156,269, dated Aug. 21, 2018 (shown in attachment 3).
Office Action Response, U.S. Appl. No. 15/156,269, dated Jul. 3, 2018 (shown in attachment 4).
Examiner Interview Summary, U.S. Appl. No. 15/156,269, dated Jul. 9, 2018 (shown in attachment 5).
Notice of Allowance and Fee(s) Due (including a Notice of Allowability section, an Examiner's Amendment section, and an Allowable Subject Matter section), U.S. Appl. No. 15/156,269, dated Oct. 30, 2018 (shown in attachment 6).
Amendment After Allowance, U.S. Appl. No. 15/156,269, dated Dec. 19, 2018 (shown in attachment 7).

WIRELESS SOIL PROFILE MONITORING APPARATUS AND METHODS

RELATED APPLICATIONS

This application claims priority to and is a continuation-in-part of application Ser. No. 15/156,269, entitled "Wireless soil profile monitoring apparatus and methods," which was filed on May 16, 2016. The foregoing application is incorporated in its entirety into this application.

DESCRIPTION

Field of the Invention

The invention relates generally to measurement devices and more specifically to measurement devices for measuring characteristics of a soil profile including volumetric water content, electrical conductivity and temperature at various depths in the soil.

BACKGROUND OF THE INVENTION

The present invention is primarily focused on taking accurate measurements of volumetric water content (VWC) in a variety of media, including but not limited to: soil, wood, concrete, building materials, clothing, and the like. This invention is useful in such applications as crop irrigation, lawn care, gardening and other landscaping applications, laundry systems, non-destructive testing for ground water infiltration into buildings, and a full range of moisture environments ranging from dry to completely saturated.

The present invention is particularly suited for big data environments such as large scale deployment of numerous sensors such as industrial irrigation systems and municipal irrigation systems because the present invention addresses the issues of accuracy and total lifecycle cost of soil monitoring devices. The incident methods are intended for but not limited to synthesis into microchips.

In relation to capturing a set of soil vital signs in a big data environment there is particular interest in the accurate measurement of volumetric water content in soil at large numbers of zones. However, this invention has wider applicability.

The present invention sets forth a low-cost, ultra-low power moisture sensor and integrated communication system to make remote wireless applications possible which utilize continuous unattended monitoring of a multiplicity of locations or zones. Further, the present invention provides for the implementation of inexpensive sensors with improved longevity, durability, security, reliability and wide spread applicability.

Measuring soil moisture content at a municipal or industrial scale is complex and includes a number of well-known problems in order to measure to an adequate level of accuracy and reproducibility at a reasonable cost. Often at the municipal and industrial level, deployment of a large number of sensors impacts the overall system cost because of the requirement to frequently replace batteries and the need to clean sensor probes to ensure adequate accuracy. In addition, the large number of sensors must work in a wide range of soil types and soil conditions from dry to fully saturated.

There are a number of known techniques for measuring soil water content including (a) Neutron probe—uses radioactive material which is expensive and is typically inaccurate in topsoil (b) Matric potential—uses low cost gypsum which has slow response and lacks durability (c) Tensiometers—require regular maintenance (d) Time Domain Reflectometer—is expensive and is only accurate up to 65% VWC (e) Capacitive—is low cost but is susceptible to electrical conductivity issues (f) Frequency—low cost but is susceptible to electrical conductivity issues and is limited in range (g) Impedance Matching—expensive and limited range.

The following references are representative of some of the known devices and techniques for measuring soil water content.

U.S. Pat. No. 7,944,220, teaches the performance of a dielectric moisture content sensor which is commonly limited by sensitivity to salinity and nutrient levels in the soil, as well as sensitivity to temperature change. This is in part due to soil non-homogeneity and variation of soil composition. Most crops are grown in soil with a salinity and nutrient level corresponding to an electrical conductivity between 60 mS/m to 400 mS/m and as high as 500 mS/m to 600 mS/m for certain crops, such as tomatoes, with soil conductivity in coastal environments up to 3,000 mS/m. Temperature also creates large variations and must be considered in any viable method. Salinity and other nutrients are the primary cause of significant deviation and must be considered. The result of these issues is that most reasonably priced solutions do not function or measure VWC above 65% water saturation.

U.S. Pat. No. 5,424,649, is representative of a common technique used in low cost sensors that have a thin dielectric coating. The dielectric coating is only partially effective at reducing sensitivity to soil conductivity which results in a moisture content sensor with sensitivity to soil conductivity and salinity. Coatings are also subject to wear and do not address the issue of charge stealing by the earth.

U.S. Pat. No. 5,859,536 is representative of common techniques in more costly sensors which use impedance matching networks. Because these techniques depend on current flow into the earth, it is naturally susceptible to conductance of soil to ambient ground.

U.S. Pat. No. 5,804,976 is a more reliable technique utilizing a transmission line and measuring propagation delay. However, this technique also suffers near total loss of signal at high saturation.

U.S. Pat. No. 7,030,630 is a moisture sensor with a capacitive moisture measuring element and method of determining air humidity describes time constants associated with a parallel resistance but is silent regarding the parasitic series resistance.

Current models and consequently the methods currently in use are effective for measuring humidity as in U.S. Pat. No. 7,030,630 but do not function in situ of greater than 65% volumetric water content material.

U.S. Pat. No. 5,730,165 teaches that if the sensor employs an RC circuit or variation thereof, the stray conduction path will rob the plate of charging current and will thus alter its apparent time constant.

Studies including the IEEE Experimental Electrical Modeling of Soil for In Situ Soil Moisture Measurement 2013 are instructive and provide a more accurate electrical model for soil over the entire range of saturation. This model, however, must be adapted to accurately represent the electrical parameters of sensors embedded in the earth.

Often the previously known sensors require battery replacement each season which is a significant limitation to large scale deployment.

Cost of the sensors and vulnerability of current sensors to tampering further prohibits wide deployment in unsecured areas.

As a result, all of the current techniques have proven uses in particular segments but they suffer at least in terms of cost, complexity or accuracy, thus preventing ubiquitous adoption for large scale data collection such as in a metropolitan or industrial sensor network.

SUMMARY OF THE INVENTION

The present invention is a volumetric water content sensor comprising an integrator circuit, switched capacitors and conductors placed in proximity of the material to be sampled.

The signal applied to the sample is transient with very high frequency components.

During each measurement only a portion of the transient response is captured by the integrator.

Additionally, at least two separate measurements may be used in combination to determine volumetric water content and electrical conductivity.

In this case, each measurement consists of generating a control signal with fixed period and different fixed duty cycle for a fixed number of cycles.

During each measurement a different portion of the transient response is captured by the integrator making it possible to extract VWC and electrical conductivity (EC).

One aspect of the invention is accounting for charge stealing by the earth in highly saturated soil. Considering in situ measurement using a three terminal model instead of two allows accurate measurement of 0% to 100% VWC media and true separation of the measurements of the permittivity and conductivity of the media, whereas conventional sensors cease to operate above 65% VWC A second aspect of the invention is measuring permittivity and EC by two measurements including a long and short sample window. A sample window is formed by timing the diverting of the electrical current between two separate sampling capacitors during successive charge events. A first measurement is made using a short window and second measurement is made using a long window. The window time is the percentage of time the first capacitor is charged compared to the charge event.

This allows for a non-galvanic connection to the media which prevents oxidation issues due to exposed metal. It also prevents electroplating issues, thus extending the life of the sensor. Unlike traditional sensors it provides a full range measurement including dry to completely saturated media.

A third aspect of the invention is aggregating thousands of individual measurement events per second in the analog hardware. This allows much greater sensitivity in completely dry soil. It also provides accuracy as a tradeoff with time. The incident method typically provides 12 bits of accuracy in less than 2 milliseconds.

A fourth aspect of the invention is the use of a transient measurement technique instead of an AC signal. This allows very high frequencies to be used resulting in measurements taken 100 times faster than traditional methods.

The components, in contrast to traditional methods, do not include inductors or expensive oscillators and are suitable for synthesis into inexpensive microelectronics.

A fifth aspect of the invention is that of detecting tamper by determining if the sensor has been unexpectedly moved or disturbed by, for example, a person or animal.

The sensor may be housed in a durable waterproof enclosure and embedded in the earth or remotely mounted to a permanent structure such as a fence post or plant trellis.

An example deployment is to directly bury the sensor in irrigation pipe trenches with antenna cable extending to sprinkler risers.

The plurality of probes can be configured to include any number of zones with individual volumes of influence, including profiling the soil for adequate drainage and migration of nutrients.

Comparisons with reference material inside the sensor removes the need for soil standards or recalibration.

The low output impedance and low input impedance provided by this method provides an important mechanism for placement of the sensor electronics up to several meters from the probes by providing shielding up to the volume of influence for each of several zones. The external antenna connection provides further reach to above ground structures and puts the sensor out of sight.

Because RF components are not used there is an associated reduction in the need for power. The reduced power consumption of the present application can provide four (4) updates per day for over six (6) years on AA batteries making it suitable for long term deployment; thus making it maintenance free for the entire lifecycle of the sensor. When combined with low cost metropolitan and industrial network radio microchips such as LoRaWan™ and SigFox™, it is suitable for public big data applications including thousands of zones over greater than a 15 Km radius and up to 1 Km in urban environments.

The sensor may be configured to measure the moisture content of soil. However, the moisture content sensor may be arranged to measure other mediums such as wood, concrete, textiles, moisture sensitive polymers, etc.

The probes may be constructed of nearly any conductive or semi conductive material and may be coated or left in contact with the media and include openings for moisture to pass freely.

An embodiment of the apparatus and method may include the moisture content/EC sensor as well as a temperature sensor to measure the temperature of the media and surrounding media, humidity sensor, rain fall sensor, light sensor, wind sensor and the like for the prediction of future change in moisture.

The invention stores reference profile data for the purpose of detecting removal or tampering of the sensor. It also includes cryptographic keys for preventing eavesdropping or man-in-the-middle attack, making it suitable for industrial and municipal applications.

The invention is advantageous for tracking the factors for, and prediction of future moisture content in the media, thus enabling more judicious use of water and when coupled with precipitation forecast information it provides the platform for ubiquitous large data collection and efficient irrigation and prevention of water damage.

In one embodiment, vertical arrangement of up to seven zones track the propagation of moisture in the media. This is advantageous to account for hysteresis and allow for creating critically damped volumetric water content in the media and prevent runoff or starvation of water. It also provides a mechanism for tracking the propagation of nutrient fertilizer through the soil. This information is used to optimize watering patterns and fertilizer patterns for various soil types and prevent undesirable runoff of bio-nutrients, which is a known cause of algae outbreaks in many lakes.

Measurement of permittivity and electrical conductivity of the media is made by successive long and short window measurements either by capturing rising edges with a short window and falling edges with a long window or by performing a series of short window events followed by a series of long window events, or any combination thereof. This allows the sensor to function in completely dry media or when completely submersed in water.

The measurement system is autonomous from the CPU. It is configured to execute N number of events then perform the analog to digital conversion and then activate the CPU. The CPU successively schedules long and short window measurements. It also schedules the other sensors such as temperature, light, humidity. After all of the data is collected, the CPU then activates the radio local oscillator and sends the data to the Internet repository, then notifies the power management timer to power off everything for a period of time, six hours.

A rapid measurement using only a very small number of events is performed periodically to detect tamper and perform rapid notification by storing and comparing against stored previous measurements.

The features discussed in relation to any of the aspects of the invention may be applied to any other of the aspects of the invention.

DETAILED DESCRIPTION OF THE INVENTION

First Embodiment

Figure 1:
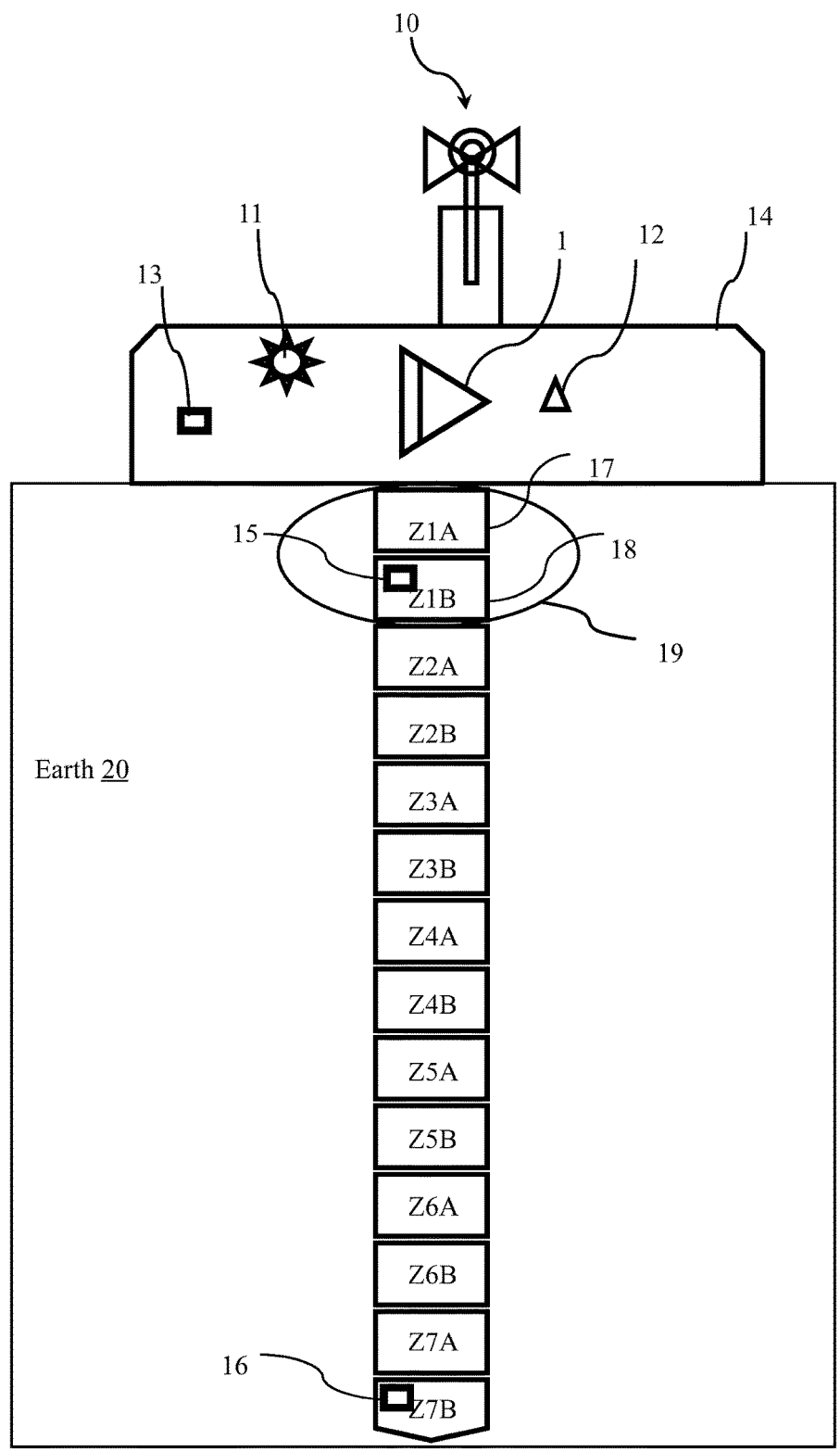
FIG. 1 is a first embodiment with vertical profile arrangement of zones.

FIG. 1 shows a volumetric water content sensor comprising an integrator circuit 1 for measuring soil moisture content. The VWC sensor measures moisture content at seven zones within the soil with each zone having a distinct volume of influence 19. A volume of influence is the space within the soil in electrical proximity of probe terminal 17 and probe terminal 18. The apparatus shown in FIG. 1 also includes a radio and radio antenna 10. The radio provides direct connection and logging of sensor data to a big data server via network including the Internet, WiFi, WiFi Max, LoRaWan™. The apparatus further includes a plurality of sensors for measuring other parameters which may be used in combination with the water content measurement for predicting soil conditions. The plurality of sensors may include: a topsoil temperature sensor 15, a root temperature sensor 16 and an air temperature sensor 13, a humidity sensor 12 and a light sensor 11. The electronics for the moisture sensor are housed in an enclosure 14. The enclosure is configured to be water proof.

The electronics in this embodiment are housed with or adjacent to the moisture probes referring to Zone 1 Probe A denoted by 17 and Zone 1 Probe B denoted by 18. Each set of probes placed adjacent or near each other form a continuous profile of moisture volumes of influence in the earth 20 over a certain depth. It should be noted that the probes may also be adjacent to the material being sampled and that the material may be any type of permeable media.

Each zone is comprised of two probes. Multiple zones are arranged together to measure a VWC and EC profile at their respective depths or locations in the medium.

Second Embodiment

Figure 2:
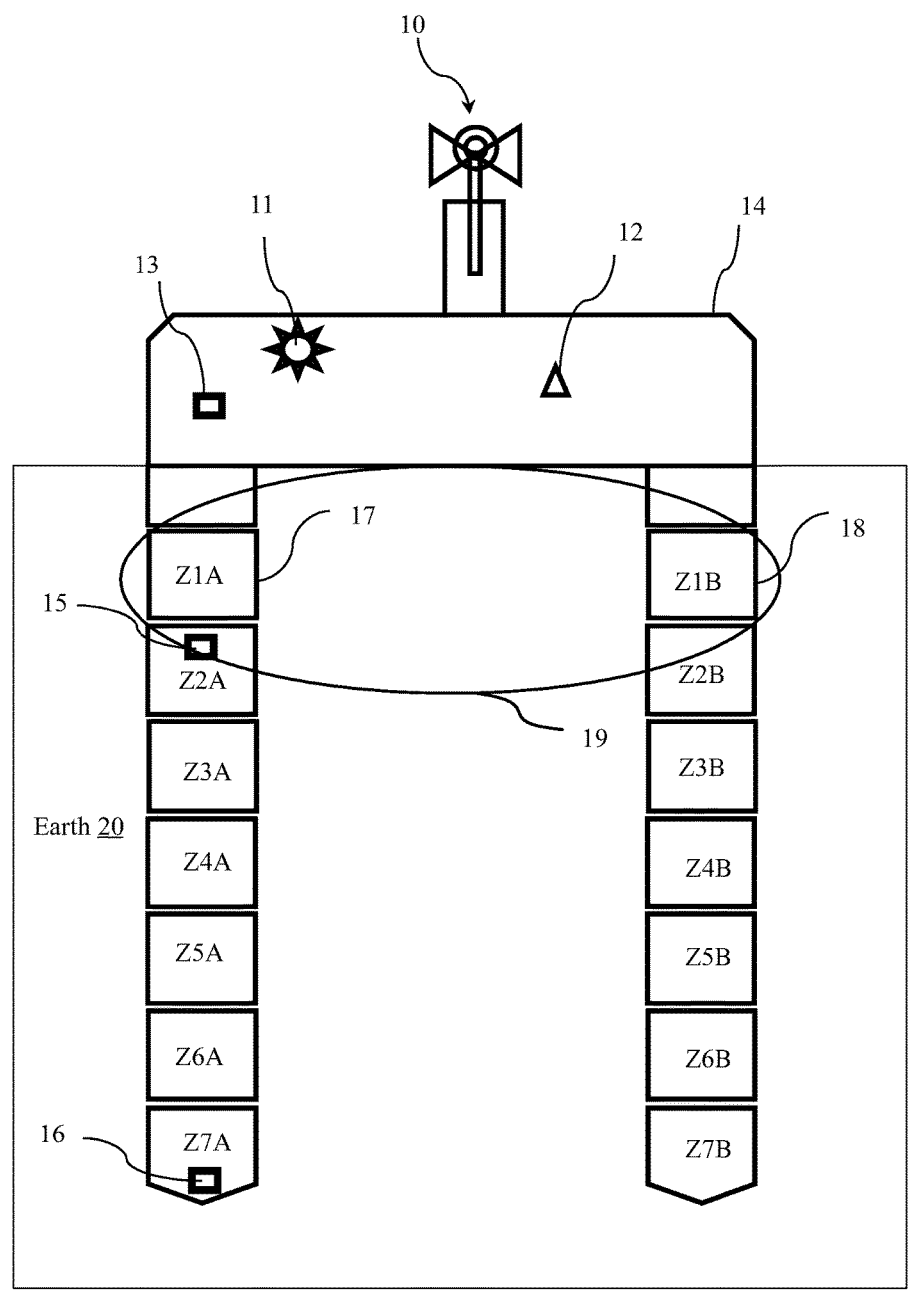
FIG. 2 is a second embodiment with an alternative zone of influence.

The second embodiment shown in FIG. 2 includes the means for measuring soil moisture content also at several levels within the soil and includes the plurality of sensors. The probes in this embodiment, however, are spaced horizontally and provide for a larger volume of influence by further separating the probes. Volumes of greater than a cubic meter can be sampled using the method of this invention. It is noted that previously available sensors measure up to only a few centimeters.

Third Embodiment

Figure 3:
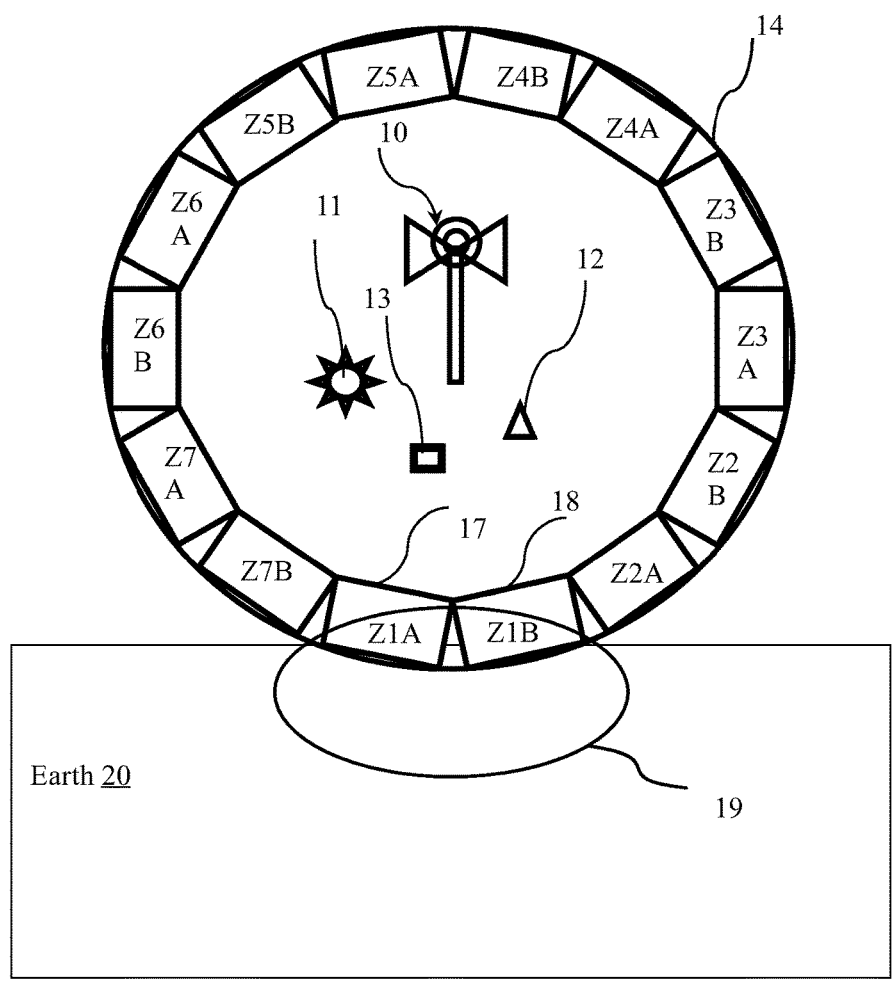
FIG. 3 is a surface profile arrangement of zones.

FIG. 3 illustrates a third embodiment which includes a means for measuring topsoil moisture content at numerous locations. The probe conductors in this embodiment are spaced around a wheel such as on the wheel of a tractor or lawn mower. Samples may be correlated with GPS coordinates to create a detailed topsoil moisture map.

Unlike traditional methods of moving a sensor above the surface or dragging a sensor across the material to be sampled, the current invention provides a consistent amount of pressure and contact with the soil.

The current apparatus is useful to reduce the issues associated with air gaps between the soil and sensor probes. The current invention also applies to radio frequency backscatter measurement of volumetric water content as well as time domain reflectometry measurement of volumetric water content.

Fourth Embodiment

Figure 4:
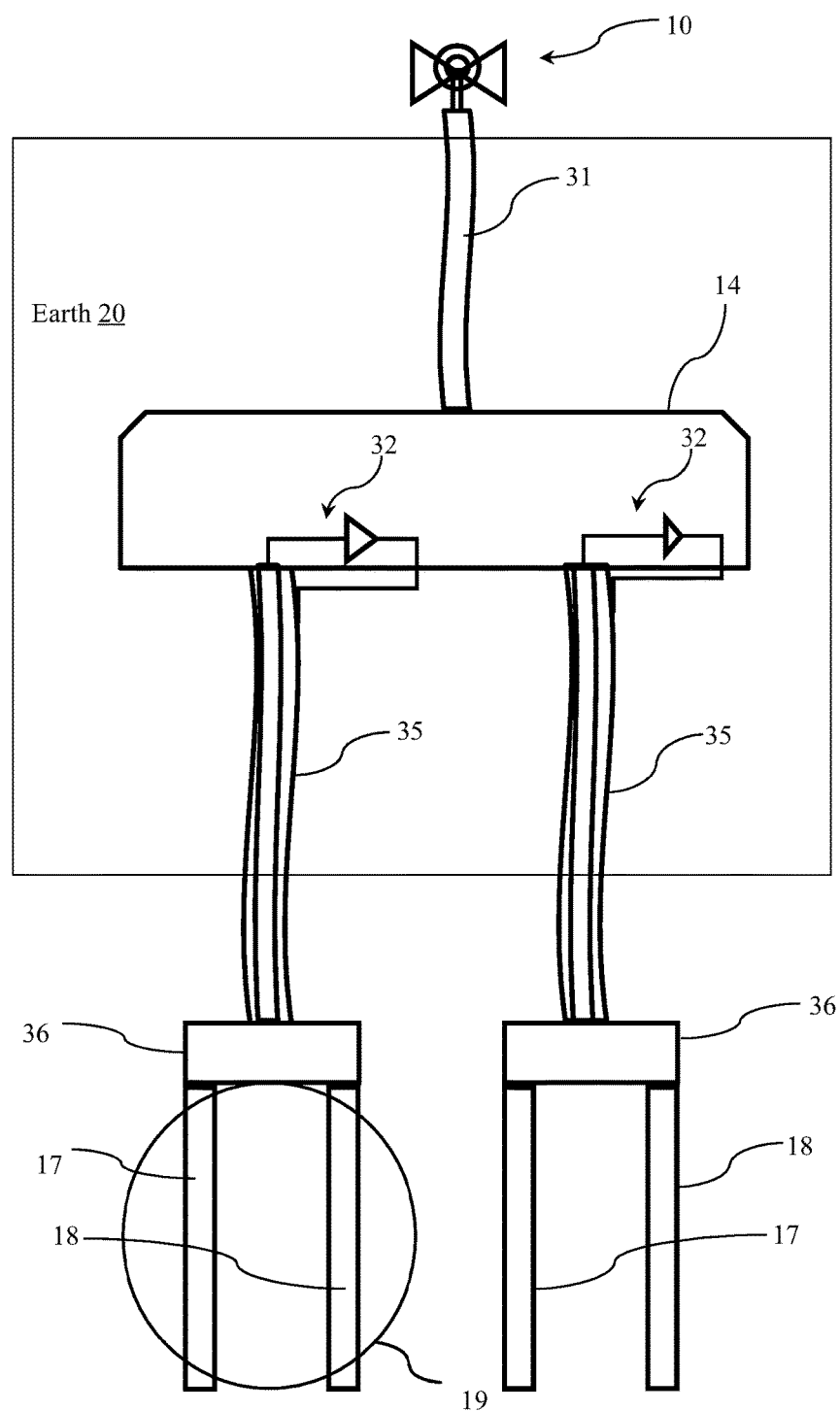
FIG. 4 is a distributed zone arrangement.

FIG. 4 illustrates a third embodiment which includes a coaxial cable 35 connection between the various probes 36 and the enclosure 14 encasing the electronics. The driver shield 32 of the coax greatly reduces the parasitic capacitance of the coaxial cable 35. Likewise the antenna 10 may be separated from the enclosure 14 using the antenna coax cable 31. This allows placement of the probes under ground level in a high traffic area and hiding the electronics from view under the ground and allowing the antenna to be housed above or at the surface of the ground in a separate casing.

The embodiments are to illustrate a few of the many possible configurations for measuring soil moisture content. It is also possible, for example, to define the zones to cover a physical volume, for example in a "square foot gardening" grow box or in separate plant containers or separate crop rows or to provide redundancy for accuracy.

Method

Figure 5:
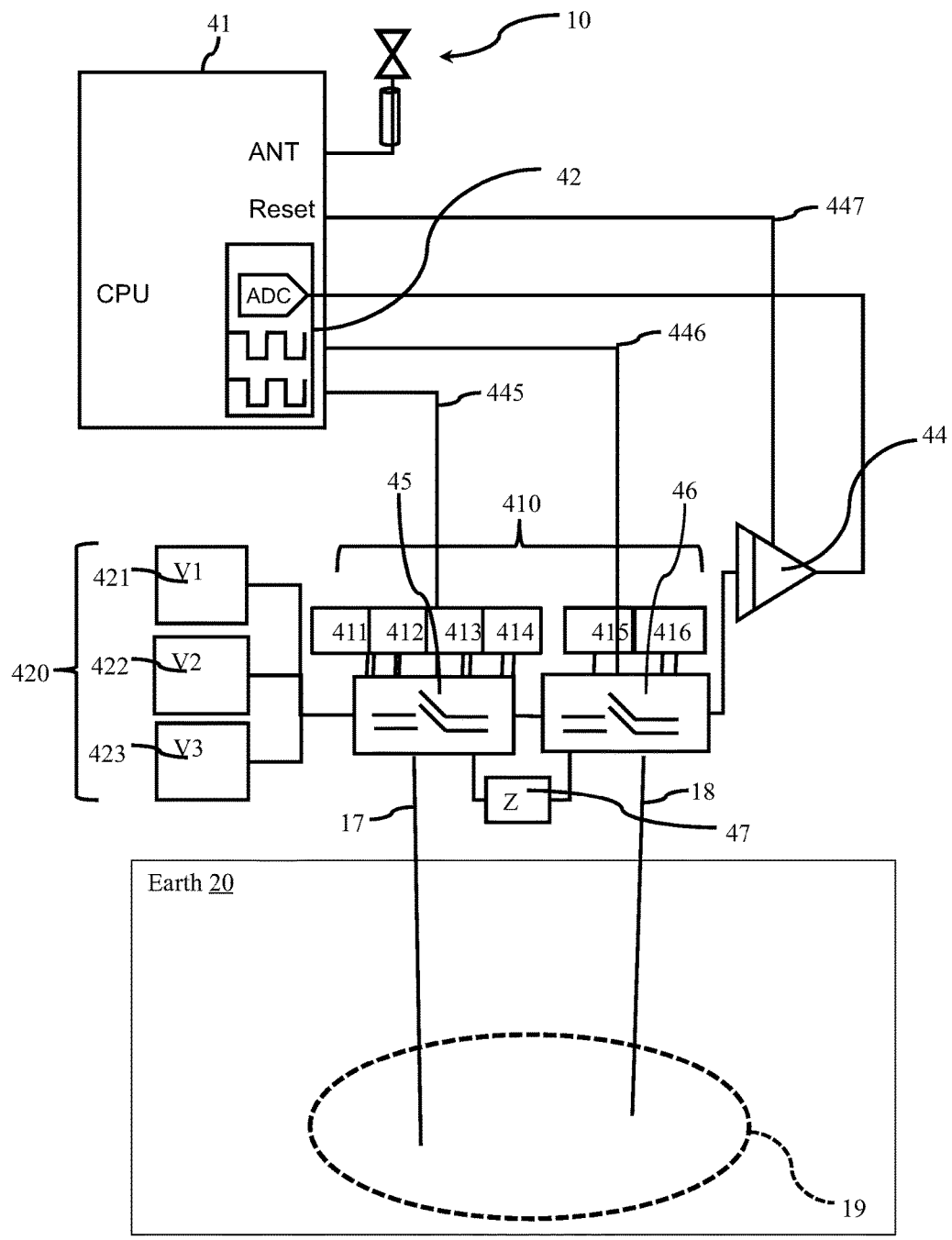
FIG. 5 is a schematic of a moisture sensor system.

FIG. 5 illustrates an electrical schematic of the moisture sensor system which provides the means of measuring soil moisture content. The electronics includes the following components: CPU or radio System On Integrated Chip (SoIC) 41; Embedded Sensor Driver module 42; Integrator 44; first bank or switches or Quad DPQT CMOS Switch 45, second bank of switches or Dual DPQT CMOS Switch 46;

Reference Impedance 47; Bank of Capacitors 410 (including Capacitors 411-416), Voltage References 421-423.

Control signals for the soil volumetric water content saturation are provided by Embedded Sensor Driver Module 42 of the CPU 41. The Embedded Sensor Driver Module 42 outputs two (2) Pulse Width Modulated (PWM) signals used to control the first bank of switches 45 associated with capacitor bank 410 (411, 412, 413, 414), and the second back of switches 46 associated with capacitor bank 410 (415, 416). The Embedded Sensor Driver Module 42 also includes an Analog to Digital Converter (ADC) to capture the output of the Integrator 44.

The measurement sequence begins by the CPU 41, creating two output signals, for example, a period of 4.4 microseconds. A first measurement, M01, is made using control signal 445, for example, at 25 percent duty cycle and control signal 446, for example, with 50 percent duty cycle.

The phase difference between signal 445 and signal 446 is made to be overlapping with signal 445 leading signal 446, for example, a 0.3 microseconds overlap. This creates a sequence of alternating phase I and phase II cycles.

During Phase I: Capacitor 411, Capacitor 415, Capacitor 412 and the probe are placed respectively in series with each other. Capacitor 416 is placed across ground Reference 423, Capacitor 413 is placed across the +5 Volt Reference 421 and −5 Volt Reference 422, and Capacitor 414 is conversely placed across −5 Volt Reference 422 and +5 Volt Reference 421.

During Phase II: Capacitor 413, Capacitor 416, Capacitor 414 and the probe are respectively placed in series with each other. Capacitor 415 is placed across the integrator and Ground Reference 423, Capacitor 411 is placed across +5 Volt Reference 421 and −5 Volt Reference 422, and Capacitor 412 is placed across −5 Volt Reference 422 and +5 Volt Reference 421.

The alternating sequence produces an alternating 20 Volt signal to appear across the probe terminals 17 and 18.

In this case, during Phase II the integrator sums the current collected in the probe during Phase I. This allows for a very short window for collecting the current in the probe during Phase I and a long time for the integration during Phase II. This allows for an inexpensive OpAmp, for example, <1 MHz Gain Bandwidth. The resulting filter response however is capable of capturing frequency components >5 MHz for vastly improved bound moisture detection.

The CPU 41 continues this sequence for a specified number of cycles, for example, 0.25 milliseconds to allow the probe to reach a nominal average common mode voltage.

The CPU 41 then releases the Reset 447 on the Integrator 44.

The CPU 41 continues this sequence for another specified or predetermined number of cycles, for example, a total of 256 cycles or 1.75 milliseconds longer. This produces a full range of 0 Volts for dry material to 2.5 Volts for 100% saturated material with very high precision in under 2 ms. For incredibly precise measurements or for an extremely large volume of influence the number of cycles can be increased to approximately 5000 cycles limited only by the input referred offset of the OpAmp.

The CPU 41 then stops both control signal 445 and control signal 446.

The CPU 41 then starts an Analog to Digital Conversion, ADC.

The CPU 41 records the ADC measurement as M01, which represents a first ("1") measurement ("M") in zone 0 ("0").

The CPU 41 then repeats the measurement sequence with control signal 445 and control signal 446 both at 50 percent duty cycle.

The CPU 41 then records the ADC measurement as M02, which represents a second ("2") measurement ("M") in zone 0 ("0") (which has, in one embodiment, a different duty cycle).

The CPU 41 then signals the switch 46 to connect the probe terminals 17 and 18 to the Reference Impedance 47.

The CPU 41 then repeats the measurement sequence with signal 445 at 25 percent duty cycle and records the ADC measurement as M11, which represents a first ("1") measurement ("M") in zone 1 ("1") (e.g., with a 25% duty cycle reflecting a reference impedance 47).

The CPU 41 then repeats the measurement sequence with signal 445 at 50 percent duty cycle and records the ADC measurement as M12, which represents a second ("2") measurement ("M") in zone 1 ("1") (e.g., with a 50% duty cycle reflecting a reference impedance 47).

The CPU 41 then signals the switch 46 to connect the probe terminals to Zone(N) and repeat the same measurement sequence to record MN1 through MN2 for each zone.

The CPU 41 then computes the raw saturation using the following steps.

The measurements MN1 and MN2 are adjusted to remove the parasitic capacitance by subtracting M01 and M02 respectively.

The measurements are then scaled to account for temperature and supply voltage variation, resulting in Mz1 (which represents a first ("1") measurement ("M") in zone z ("z") with "z" representing the pertinent zone with the measurement adjusted and scaled) and Mz2 (which represents a second ("2") measurement ("M") in zone z ("z") with "z" representing the pertinent zone with the measurement adjusted and scale), e.g., by multiplying by the scaling factor based on M11 and M12 from the 50 percent reference 47.

Saturation for each zone is then extracted based on the ratio of the duty cycles. For example with 25% and 50% using the formula, Saturation=(2*Mz1−Mz2)*100%.

Electrical Conductivity for each zone is then extracted using the formula EC=(2*Mz2−Mz1)

Figure 8:
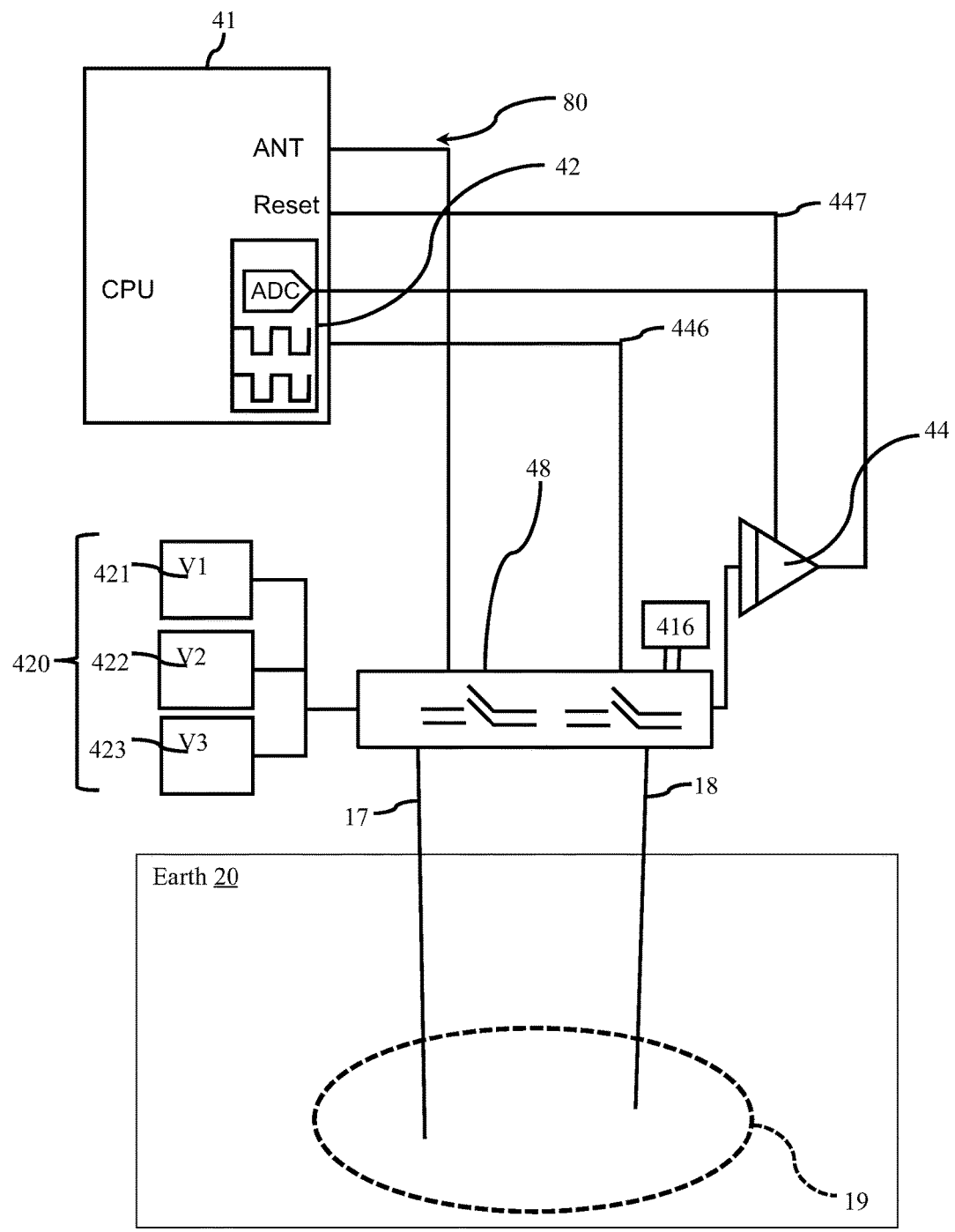
FIG. 8 is a schematic of a cost reduced moisture sensor system.

FIG. 8 illustrates an electrical schematic of a cost reduced moisture sensor system comprising an antenna 80 that also uses a method which provides the means of measuring soil moisture content. The electronics include: CPU or radio System On Integrated Chip (SoIC) 41; Embedded Sensor Driver module 42; Integrator 44; bank of switches or Dual DPQT CMOS Switch 48; Capacitor 416, Voltage References 421-423.

In the cost reduced sensor system, the overlapping control signals that provided the make before break connections are replaced with a single control signal and a single switch bank of the type break before make. These replace the need for the phase difference between overlapping signal 445 and signal 446.

This measurement sequence of alternating phase I and phase II cycles is the same as before with separation of the phases being provided by the break before make switches instead of overlapping signals during Phase I and Phase II as follows.

During Phase I: The probes are placed in series with the +5 Volt Reference 421 and Ground Reference 423. Capacitor 416 is placed across the integrator and Ground Reference 423.

During Phase II: The probes are placed in series with Capacitor 416.

Alternatively, During Phase I: The probes are placed on Ground Reference 423. Capacitor 416 is placed across integrator 44 with reference set to the +5 Volt Reference 421 and Ground Reference 423.

During Phase II: The probes are placed in series with the Capacitor 416.

Likewise, using an integrator 44 with sufficient bandwidth;

During Phase I: The probes are placed on Ground Reference 423.

During Phase II: The probes are placed directly across the integrator 44.

Improved accuracy can be achieved by adjustments to the formula ratio as necessary based on actual measured window sizes for individual apparatus embodiments. Generally, simply using the control signal duty cycle ratio produces better than 2% accuracy at nominal temperatures.

The sequences described herein are only specific representations of the method of using different window sizes to extract saturation and electrical conductivity. The method applies more generally to using different window sizes.

For example a single capacitor may be successively applied to the probe terminals and the probe terminals being successively shorted together while the capacitor is placed across the integrator configured to a reference voltage. Likewise, a pair of capacitors may be successively applied to the probe and an integrator. In each case at least two different measurements are made using different window sizes.

Regarding wireless soil profile measurements being controlled by a Radio System on Integrated Chip (CPU). The Radio CPU wakes up periodically such as four (4) times a day and performs the tasks of making measurements from the various sensors typically by issuing commands via an I2C bus. The Radio CPU also provides the necessary functions for making a moisture measurement. Once it has collected the soil profile data including temperature, humidity, light level, saturation, and electrical conductivity it powers up the radio module and sends the data via LoRaWan™, SigFox™, WiFi or other modulation scheme to an Internet based big data cloud service or private database. The service combines the data with other sensor data and satellite and forecast data and applies heuristics to the data and issues updates and demands for irrigation.

Example

Measurements were taken on soil samples of white clay with various amounts of water content using the example values presented above.

Saturation is defined as the ratio of volume of water to the total volume of space or voids in the soil. The samples were independently measured using density of water 1 g/cc and the density of air dried white clay 0.97 g/cc to have the Saturations of 7%, 25%, 37%, 38%, 55%, 72%, and 89%.

Figure 6:
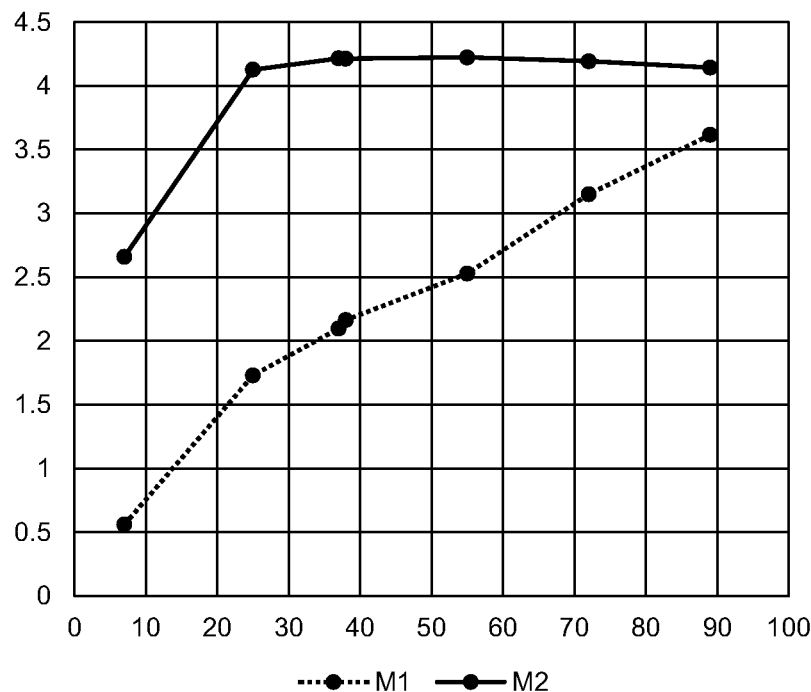
FIG. 6 is a graph containing example measurement data.

Examination of FIG. 6 shows the ADC measurement values of each of the samples electrical models using two different window sizes; M1, which represents a first ("1") measurement ("M") in the pertinent zone, for example, of 0.55 microseconds and M2, which represents a second ("2") measurement ("M") in the pertinent zone, for example, of 2.0 microseconds. The measurements were taken with a duration of 2 milliseconds using a 20 Volt peak to peak stimulus with period of 4.4 microseconds.

Extraction of Saturation was accomplished using the formula Saturation=2M1−M2. The calibration measurement of zone "None" is used to offset parasitic capacitance of the apparatus. Zone "Ref" is used to map the Saturation to Percent Volumetric Water Content. This formula is based generally on the windows sizes of 0.55 microseconds and 2.0 microseconds. The equation used may be adapted to address specific window sizes and other patristics of the apparatus or environment as necessary such as when in containers or varying temperature and the like.

Figure 7:
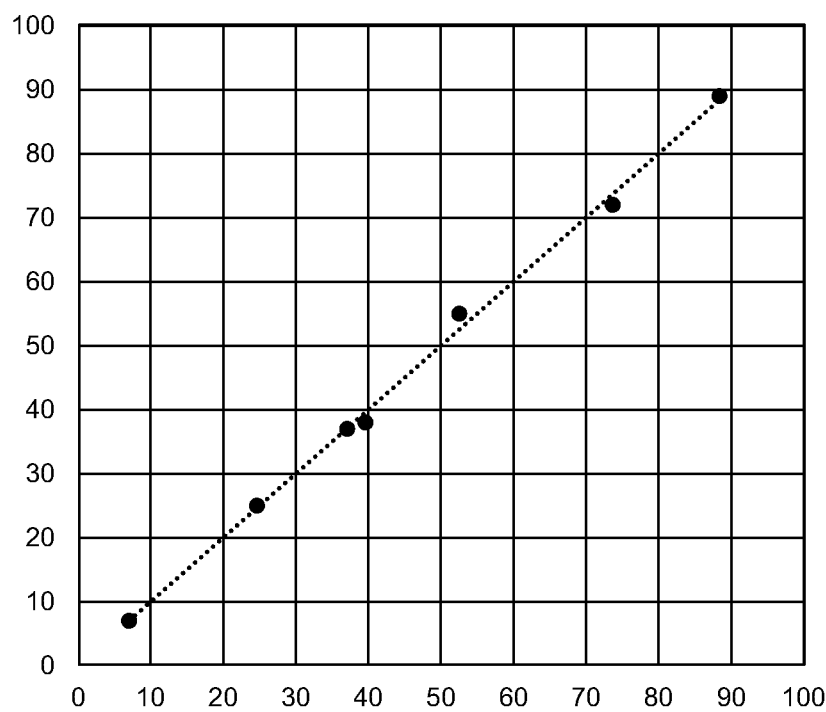
FIG. 7 is an accuracy comparison of example measurements.

FIG. 7 shows the Measured Saturation vs the Gravimetric Computed Saturation in this example. The results agree within 2% over the entire range of very dry to completely saturated white clay.

A final aspect of the invention is the dual use of the probes as antenna as shown in FIG. 8.

During transmission of the moisture data the antenna output is connected by the bank of switches or Dual DPQT CMOS Switch 48 to one or more of the probes.

Alternately, an RF diplexer may be used to connect the antenna output to the probe.

An important aspect of the invention is the tuning of the antenna according to the moisture measurement. Tuning is accomplished by using the calculated permittivity [based on moisture content of the soil] during the moisture sensing phase.

The probes are configured using the switch bank and physically oriented to form a wide band antenna suitable for transmission in, for example, dry and highly saturated soil such as shown in FIG. 2.

Alternatively, if the radio transmission is of sufficiently high frequency an RF diplexer or duplexer of suitable performance can be used instead of the switch bank to attach the radio output to the probe terminals.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed is:

1. A method for measuring characteristics of a material by an apparatus, comprising:
    performing a set of measurement sequences, wherein each measurement sequence comprises:
        generating, for a plurality of cycles, a control signal;
        applying, for the plurality of cycles, the control signal to a switch bank that is coupled to a capacitor; and
        aggregating, by an integrator for the plurality of cycles, a current of the capacitor, wherein the current is collected when the capacitor is coupled in series with a probe;
    measuring, for the set of measurement sequences, an output of the integrator to produce a set of measurements, wherein the set of measurements comprises a first measurement taken with the control signal having a first duty cycle and a second measurement taken with a second duty cycle that is different from the first duty cycle;
    determining a saturation based on the first measurement, the second measurement, and a ratio of the first duty cycle and the second duty cycle; and
    transmitting data indicating the saturation.

2. The method of claim 1, wherein the material is soil.

3. The method of claim 1, wherein transmitting the data comprises communicating, by wireless transmission, the data indicating the saturation to a server or database.

4. The method of claim 1, wherein each of the plurality of cycles produces an alternating 20 volt signal across terminals of the probe.

5. The method of claim 1, wherein the control signal has a 25% duty cycle for a first measurement sequence, and wherein the control signal has a 50% duty cycle for a second measurement sequence.

6. The method of claim 1, wherein the probe functions as antenna for transmission of moisture data.

7. The method of claim 6, wherein the probe is tuned to operate as a wide band antenna suitable for transmission in a wide variety of moisture conditions.

8. The method of claim 1, wherein the data indicating the saturation is used to tune an antenna.

9. The method of claim 1, further comprising using the probe as an antenna.

10. A method for measuring characteristics of a material by an apparatus, comprising:
    performing a set of measurement sequences, wherein each measurement sequence comprises:
        aggregating, by an integrator for a plurality of cycles of a control signal, a current in series with a probe;
        measuring, for the set of measurement sequences, an output of the integrator to produce a set of measurements, wherein the set of measurements comprises a first measurement taken with the control signal having a first duty cycle and a second measurement taken with a second duty cycle that is different from the first duty cycle;
    determining a saturation based on the first measurement, the second measurement, and a ratio of the first duty cycle and the second duty cycle; and
    transmitting data indicating the saturation.

11. The method of claim 10, wherein the material is soil.

12. The method of claim 10, wherein transmitting the data comprises communicating, by wireless transmission, the data indicating the saturation to a server or database.

13. The method of claim 10, wherein each of the plurality of cycles produces an alternating 20 volt signal across terminals of the probe.

14. The method of claim 10, wherein the control signal has a 25% duty cycle for a first measurement sequence, and wherein the control signal has a 50% duty cycle for a second measurement sequence.

15. The method of claim 10, wherein the probe functions as antenna for transmission of moisture data.

16. The method of claim 15, wherein the probe is tuned to operate as a wide band antenna suitable for transmission in a wide variety of moisture conditions.

17. The method of claim 10, wherein the data indicating the saturation is used to tune an antenna.

18. The method of claim 10, further comprising using the probe as an antenna.

* * * * *